US012643854B2

(12) United States Patent
Tesson et al.

(10) Patent No.: US 12,643,854 B2
(45) Date of Patent: Jun. 2, 2026

(54) PROCESS FOR PREPARING A CRYSTALLINE FORM OF FLUVASTATIN SODIUM SALT

(71) Applicant: F.I.S.—FABBRICA ITALIANA SINTETICI S.P.A., Montecchio Maggiore (IT)

(72) Inventors: Nicolas Tesson, Barcelona (ES); Montserrat Trilla Castaño, Barcelona (ES); Riccardo Motterle, Montecchio Maggiore (IT); Paolo Stabile, Montecchio Maggiore (IT)

(73) Assignee: F.I.S.—FABBRICA ITALIANA SINTETICI S.P.A., Montecchio Maggiore (IT)

( * ) Notice: Subject to any disclaimer, the term of this patent is extended or adjusted under 35 U.S.C. 154(b) by 338 days.

(21) Appl. No.: 18/603,896

(22) Filed: Mar. 13, 2024

(65) Prior Publication Data

US 2024/0317684 A1 Sep. 26, 2024

(30) Foreign Application Priority Data

Mar. 21, 2023 (EP) .................................... 23163236

(51) Int. Cl.
*C07D 209/18* (2006.01)

(52) U.S. Cl.
CPC .................................. *C07D 209/18* (2013.01)

(58) Field of Classification Search
None
See application file for complete search history.

(56) References Cited

U.S. PATENT DOCUMENTS 7,368,581 B2 5/2008 Frenkel et al.

FOREIGN PATENT DOCUMENTS

WO 2004113291 A2 12/2004
WO 2004113292 A2 12/2004
WO 2005040113 A1 5/2005

OTHER PUBLICATIONS

European Search Report for Corresponding European Application No. 23163236.5 (8 Pages) (Jul. 21, 2023).

*Primary Examiner* — Adam C Milligan
*Assistant Examiner* — Jason M. Nolan
(74) *Attorney, Agent, or Firm* — LUCAS & MERCANTI, LLP

(57) ABSTRACT

A process for the preparation of a crystalline form of fluvastatin sodium salt, and a Fluvastatin sodium salt crystalline form.

10 Claims, 11 Drawing Sheets

PROCESS FOR PREPARING A CRYSTALLINE FORM OF FLUVASTATIN SODIUM SALT

CROSS-REFERENCE TO RELATED APPLICATION

This application claims the benefit of priority from European Patent Application No. EP23163236.5, filed 21 Mar. 2023, the contents of which is incorporated herein by reference.

FIELD OF THE INVENTION

The present invention refers to an improved process for the preparation of a crystalline form of Fluvastatin sodium salt. Moreover, it is also related to a novel Fluvastatin sodium salt crystalline form and a process for the preparation thereof.

BACKGROUND OF THE INVENTION

Fluvastatin (abbreviated FLV) is a member of the statin drug class, used to treat hypercholesterolemia and to prevent cardiovascular disease. Its commercial form is the sodium salt of Formula (I) (CAS 93957-55-2, abbreviated FLVNa) of the racemic mixture.

(I)

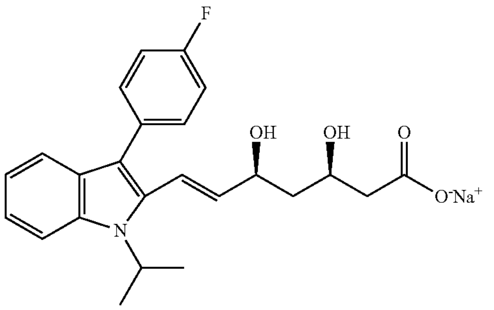

According to the literature, at least 116 crystalline forms of FLVNa are described, all of them being hydrates forms with water content ranging within 2-32% wt.

Among the various crystalline forms disclosed in the prior art, particular reference is made to FLVNa Form XIV described in patent publication WO2004/113291.

FLVNa Form XIV XRPD pattern is depicted in FIG. 1 and FLVNa Form XIV diagnostical peaks expressed in 2-Theta values (2θ) are reported in Table 1 below.

TABLE 1

Fluvastatin sodium salt crystalline Form XIV

| Angle (2-Θ° ± 0.2) | Intensity (%) |
|---|---|
| 3.7 | 69 |
| 11.2 | 51 |
| 14.9 | 22 |
| 15.9 | 28 |
| 17.9 | 100 |
| 18.4 | 84 |
| 21.8 | 68 |
| 25.7 | 40 |

Another FLVNa crystalline form, described in the literature in patent document WO2004/113292 and referred to as FLVNa Form LXXXI, is characterized by the XRPD pattern depicted in FIG. 2 and FLVNa Form LXXXI diagnostical peaks expressed in 2-Theta values (2θ) are reported in Table 2 below.

TABLE 2

Fluvastatin sodium salt crystalline Form LXXXI

| Angle (2-Θ° ± 0.2) | Intensity (%) |
|---|---|
| 3.8 | 89 |
| 11.3 | 100 |
| 15.0 | 22 |
| 15.9 | 25 |
| 17.8 | 68 |
| 18.3 | 62 |
| 21.7 | 49 |
| 25.6 | 34 |

Said FLVNa XIV and FLVNa LXXXI forms were found to be almost identical, as put in evidence by the XRPD patterns comparison depicted in FIG. 3. If comparing the 2-Theta values (2θ) diagnostic peaks reported in Table 1 for FLVNa Form XIV and in Table 2 for FLVNa Form LXXXI, in fact, it can be demonstrated that the two forms are equivalent, since the differences in 2-Theta values (2θ) are comprised in the instrument uncertainty that is ±0.2 in 2-Theta values (2θ).

The existence of so many FLVNa crystalline forms and the ease of interconversion among them caused by minimal condition variation makes very challenging the objective of the present invention, which is the development of a robust and reliable preparation method to obtain FLVNa Form XIV (or equivalent LXXXI Form).

Several examples of FLVNa Form XIV preparations are described in the literature, for example in PCT 2004/113291 and U.S. Pat. No. 7,368,581 starting from different materials:

FLVNa (Ex 1, 6, 7, 8, 9, 10, 11, 13, 14, 15, 16, 17, 19 and 20)

FLV methyl ester (Ex 2, 3, 4 and 5)

FLV tert-butyl ester (Ex 18, 21, 22, 23, 24, 25, 26 and 27)

Said preparation methods, however, face reproducibility and robustness issues and their application can result in isolating FLVNa with a crystalline form different from FLVNa Form XIV (or equivalent Form LXXXI).

Moreover, even when the desired FLVNa Form XIV (or equivalent Form LXXXI) is obtained by applying the literature procedures mentioned above, the drying operation required to remove the organic solvents from the wet material often results in the conversion of said FLVNa Form XIV (or equivalent Form LXXXI) into a different crystalline form, due to the variation of water content, temperature and relative humidity produced by the drying itself.

SUMMARY OF THE INVENTION

Therefore, the problem addressed by the present invention is to provide a process capable of producing Fluvastatin sodium salt crystalline form characterized by X-ray powder diffraction with diagnostical peaks expressed in 2-Theta values (2θ) at 3.7±0.2, 11.2±0.2, 14.9±0.2, 15.9±0.2, 17.9±0.2, 18.4±0.2, 21.8±0.2, 25.7±0.2 (Form XIV or equivalent Form LXXXI) in a robust and reliable way.

This problem is solved by a specific preparation process involving the recrystallization of Fluvastatin sodium salt of whatever crystalline form in an acetonitrile/water mixture followed by an innovative isolation protocol characterized in that the wet material is firstly washed with an organic solvent, then dried under vacuum and finally submitted to a re-equilibration step at controlled temperature and controlled relative humidity.

Recrystallization of Fluvastatin sodium salt as per the present invention preferably produces as wet material after isolation a crystalline form of Fluvastatin sodium salt not yet described in the literature, characterized by the X-ray powder diffraction pattern with diagnostical peaks expressed in 2-Theta values (2θ) at 6.9±0.2, 8.6±0.2, 12.0±0.2, 13.1±0.2, 17.7±0.2, 18.2±0.2 (refer to Table 3 and to FIG. 4).

TABLE 3

| Fluvastatin sodium salt crystalline Form similar to Form B | |
|---|---|
| Angle (2-Θ° ± 0.2) | Intensity (%) |
| 6.9 | 10 |
| 8.6 | 10 |
| 12.0 | 100 |
| 13.1 | 12 |
| 17.7 | 19 |
| 18.2 | 13 |

Said Fluvastatin sodium salt crystalline form, namely Fluvastatin sodium salt Form similar to Form B, is characterized in that it is easily and reliably converted into Fluvastatin sodium salt Form XIV (or equivalent Fluvastatin sodium salt Form LXXXI) by applying the washing, drying and re-equilibration process which is the object of the present invention.

This Fluvastatin sodium salt Form similar to Form B shows a XRPD pattern similar to that of a Fluvastatin sodium salt crystalline form already described in the literature, which is characterized by the X-ray powder diffraction pattern with diagnostical peaks expressed in 2-Theta values (2θ) at 4.1±0.2, 12.1±0.2, 12.9±0.2, 15.7±0.2, 16.3±0.2, 19.6±0.2, 20.4±0.2, 22.6±0.2 (refer to Table 4 below and FIG. 5), namely Fluvastatin sodium salt Form B.

TABLE 4

| Fluvastatin sodium salt crystalline Form B | |
|---|---|
| Angle (2-Θ° ± 0.2) | Intensity (%) |
| 4.1 | 52 |
| 12.1 | 73 |
| 12.9 | 100 |
| 15.7 | 45 |
| 16.3 | 24 |
| 19.6 | 37 |
| 20.4 | 37 |
| 22.6 | 25 |

Despite their XRPD pattern is similar, Fluvastatin sodium salt crystalline Form B and Fluvastatin sodium salt crystalline Form similar to Form B are distinct and distinguishable crystalline forms (refer to FIG. 6).

Moreover, Fluvastatin sodium salt Form B and Fluvastatin sodium salt Form similar to Form B show a different behaviour when submitted to the same temperature and humidity conditions. In particular, while Fluvastatin sodium salt Form similar to Form B can be easily converted to Fluvastatin sodium salt Form XIV (or equivalent Form LXXXI) by applying the process object of the present invention, Fluvastatin sodium salt Form B cannot be converted into Fluvastatin sodium salt Form XIV.

It follows that Fluvastatin sodium salt Form similar to Form B can be used to produce Fluvastatin sodium salt Form XIV (or equivalent Form LXXXI).

DETAILED DESCRIPTION OF THE INVENTION

Figure 1:
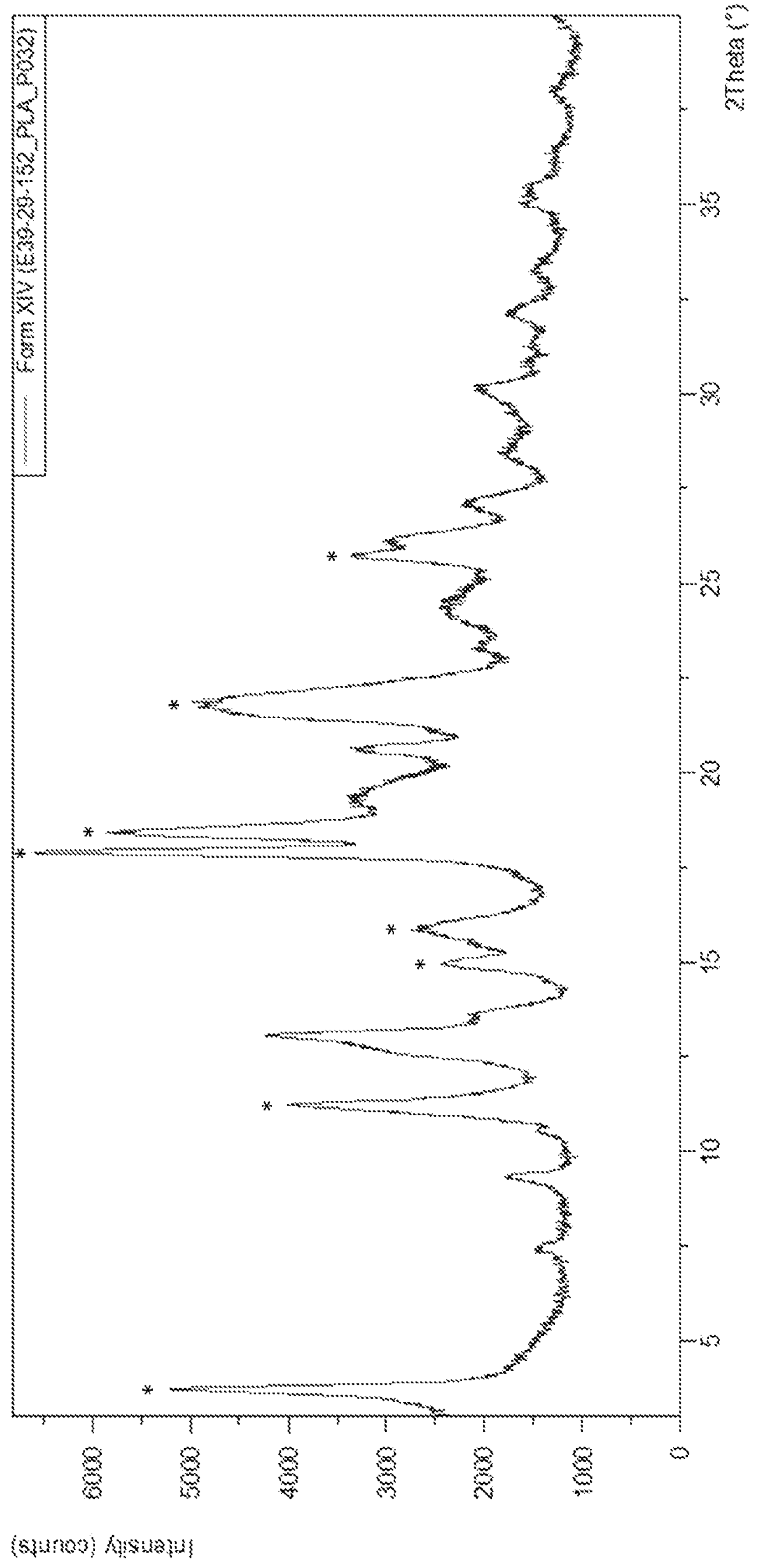
FIG. 1: XRPD diffractogram of Fluvastatin sodium salt Form XIV.
Figure 2:
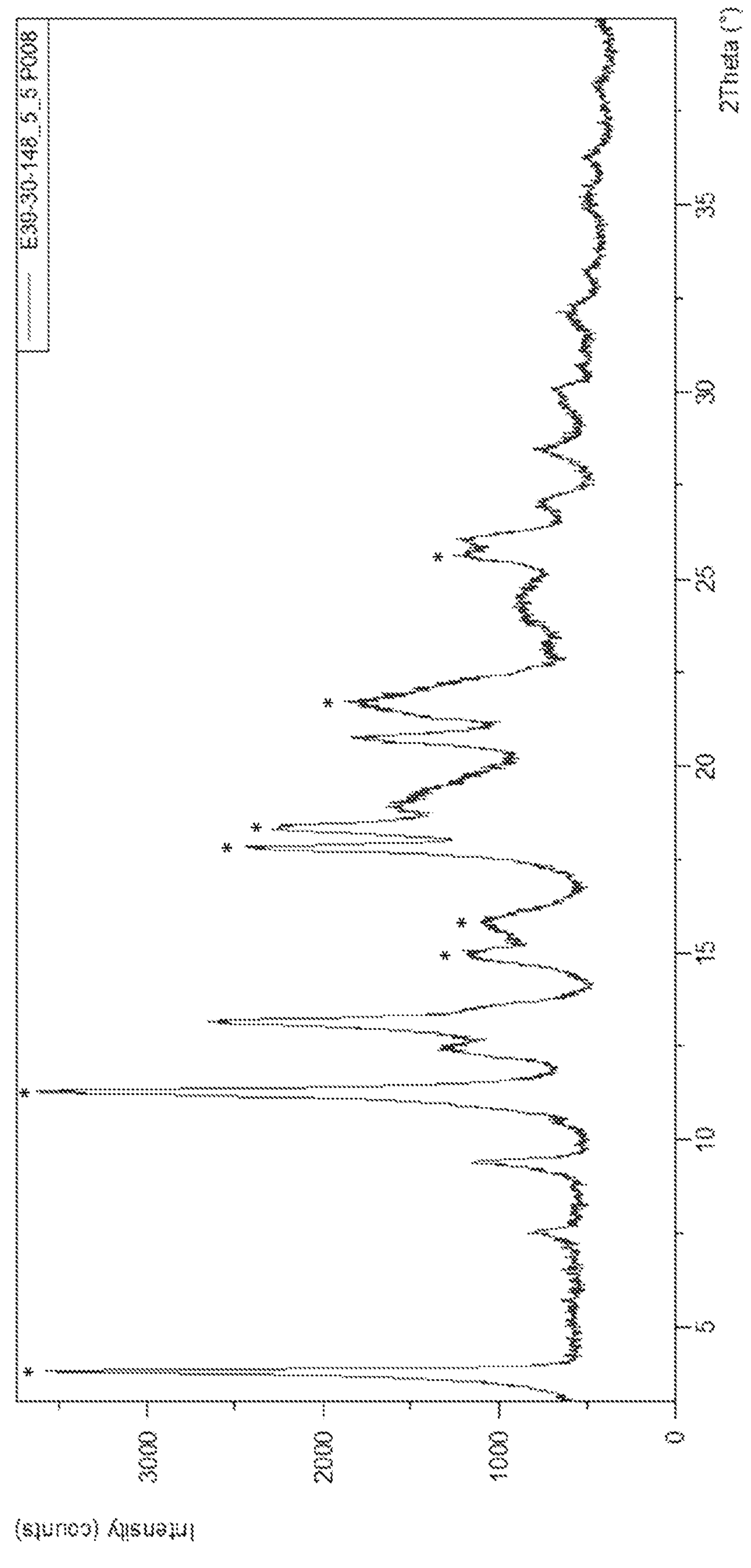
FIG. 2: XRPD diffractogram of Fluvastatin sodium salt Form LXXXI.
Figure 3:
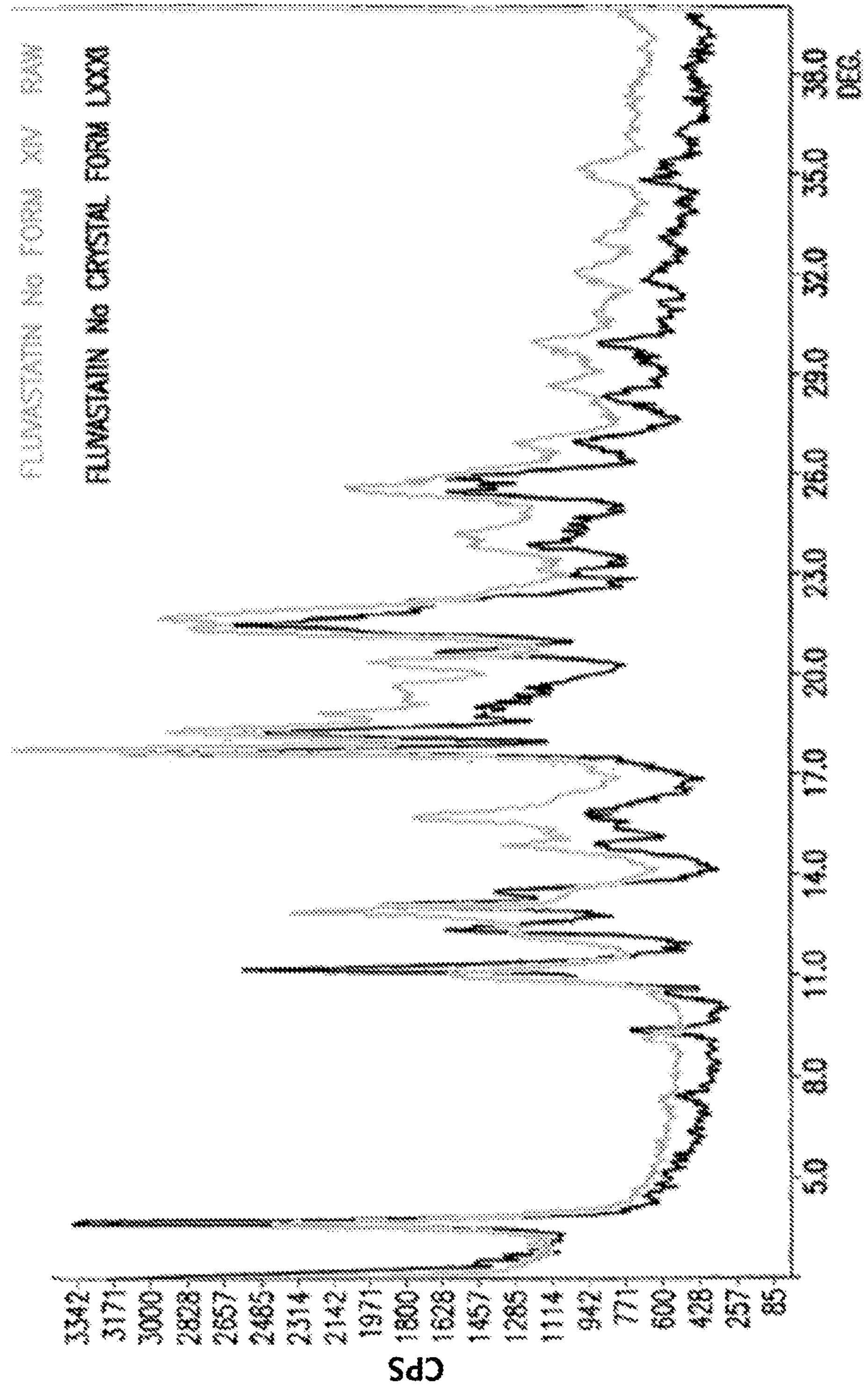
FIG. 3: XRPD comparison of the diffractograms of Fluvastatin sodium salt Form XIV (in grey) with Fluvastatin sodium salt Form LXXXI (in black) described in the literature.
Figure 4:
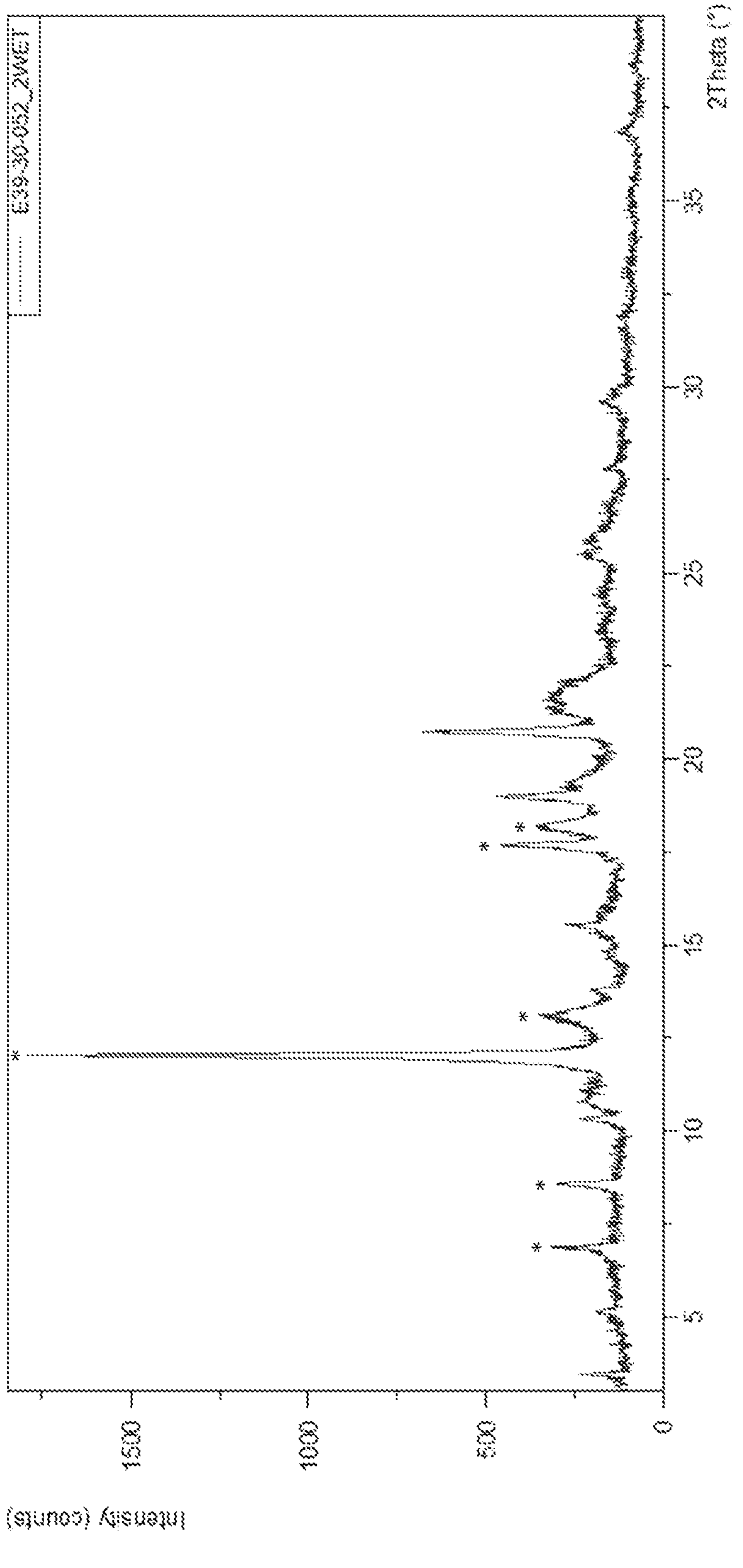
FIG. 4: XRPD diffractogram of Fluvastatin sodium salt Form similar to Form B.
Figure 5:
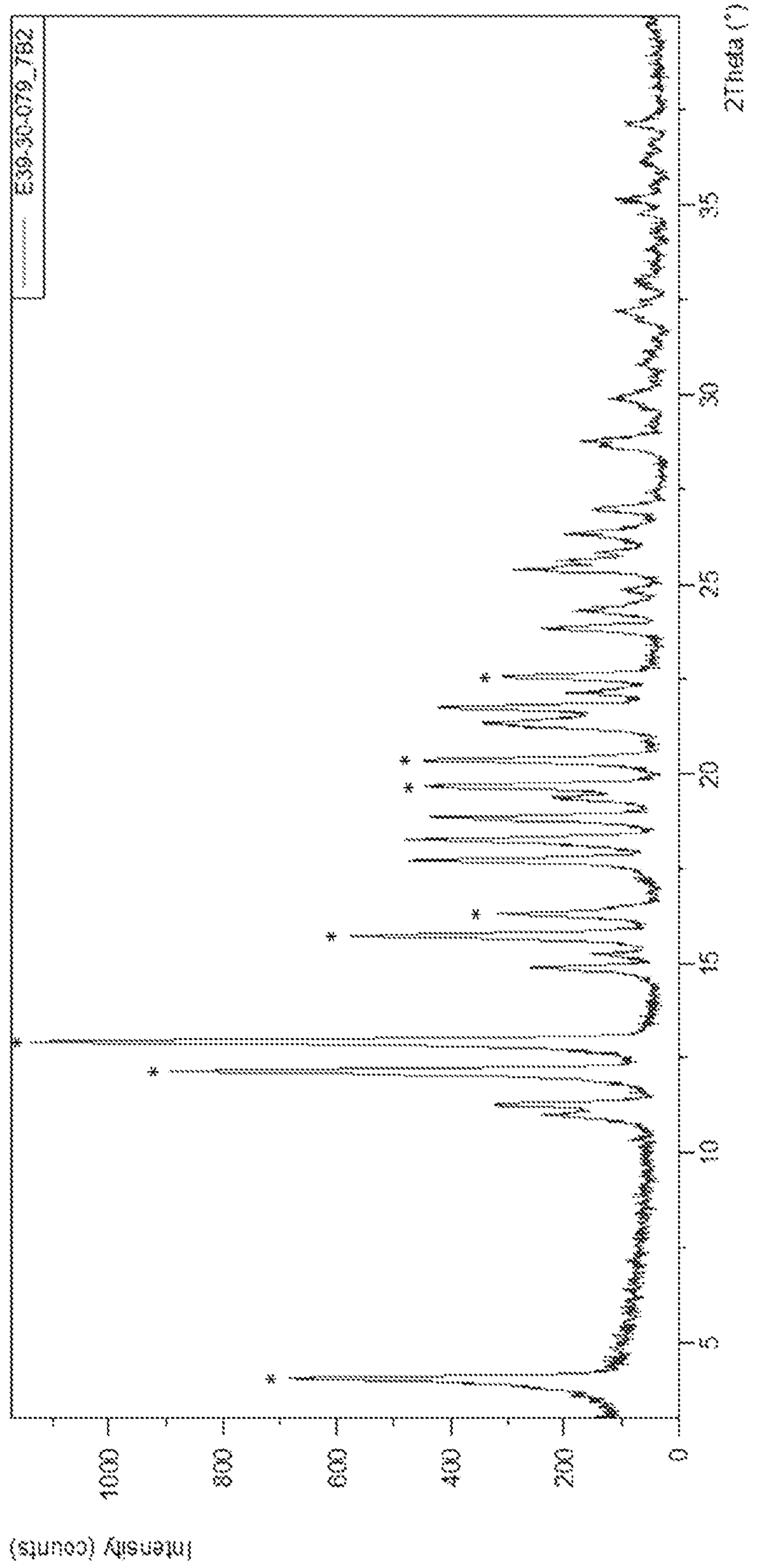
FIG. 5: XRPD diffractogram of Fluvastatin sodium salt Form B.
Figure 6:
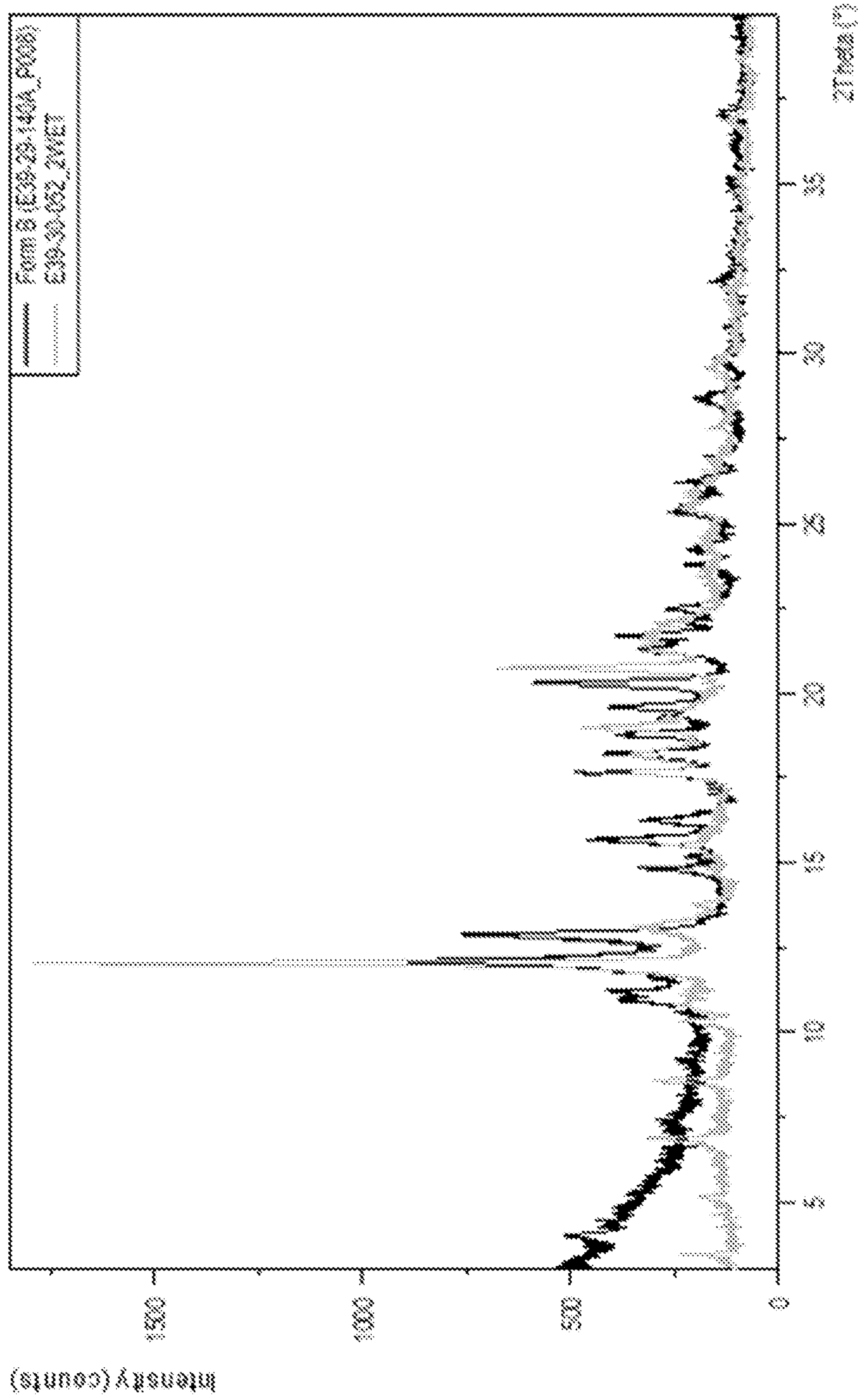
FIG. 6: XRPD comparison of the diffractograms of Fluvastatin sodium salt Form B (in black) and Fluvastatin sodium salt Form similar to Form B (in grey).

According to a first aspect, the present invention relates to a process for preparing the compound of Formula (I):

Formula (I)

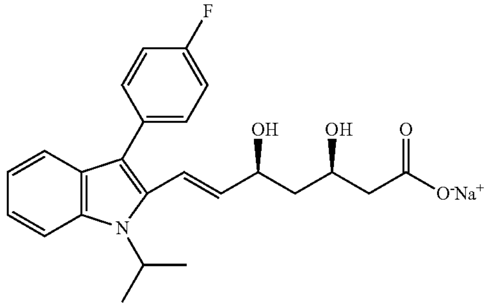

known by its chemical name (±)-7-(3-(4-fluorophenyl)-1-(1-methyl ethyl)-1H-indol-2-yl)-3,5-dihydroxy-6-heptenoic acid monosodium salt and also known as Fluvastatin Sodium salt, wherein said crystalline form of Fluvastatin sodium salt is characterized by X-ray powder diffraction pattern with diagnostical peaks expressed in 2-Theta values (2θ) at 3.7±0.2, 11.2±0.2, 14.9±0.2, 15.9±0.2, 17.9±0.2, 18.4±0.2, 21.8±0.2, 25.7±0.2 comprising or consisting in the following steps:

a) dissolving Fluvastatin Sodium salt of any crystalline form and/or amorphous form by heating the solid in a mixture of acetonitrile/water from 20/1 to 20/2.5 v/v, or alternatively in a mixture of acetonitrile/water from 5/1 to 5/2 v/v followed by dilution with acetonitrile to realize a final solvent ratio acetonitrile/water from 20/1 to 20/2.5 v/v;

b) cooling the solution to a temperature comprised in the range from 65° C. to 35° C. to promote Fluvastatin sodium salt crystallization, optionally seeding the mixture with the crystalline form of Fluvastatin sodium salt characterized by X-ray powder diffraction pattern with diagnostical peaks expressed in 2-Theta values (2θ) at 3.7±0.2, 11.2±0.2, 14.9±0.2, 15.9±0.2, 17.9±0.2, 18.4±0.2, 21.8±0.2, 25.7±0.2;

c) further cooling the mixture to a temperature comprised in the range from 35° C. to 15° C. and stirring the slurry at this temperature to complete crystallization for a period comprised from 1 hour to 3 days;

d) isolate Fluvastatin sodium salt wet material by filtration or centrifugation, wherein said Fluvastatin sodium salt has a crystalline form optionally characterized by X-ray powder diffraction diagnostical peaks expressed in 2-Theta values (2θ) at 6.9±0.2, 8.6±0.2, 12.0±0.2, 13.1±0.2, 17.7±0.2, 18.2±0.2;

characterized in that the process comprises the following further steps:

e) washing of the wet material obtained in step d) with acetonitrile, $C_1$-$C_4$ alcohol solvents or non-polar solvents;

f) drying the wet solid obtained in step e) under vacuum with a residual pressure range comprised between 1 mbar and 500 mbar at a temperature comprised in the range from 20° C. to 60° C. for a time ranging from 1 hour to 3 days;

g) re-equilibrate the crystalline form obtained in step f) by treating the solid for a time comprised between 1 hour and 11 days at a temperature comprised in the range from 15° C. to 35° C. under relative humidity (RH) comprised in a range between 40% and 80% to provide Fluvastatin sodium salt in a crystalline form characterized by X-ray powder diffraction diagnostical peaks expressed in 2-Theta values (2θ) at 3.7±0.2, 11.2±0.2, 14.9±0.2, 15.9±0.2, 17.9±0.2, 18.4±0.2, 21.8±0.2, 25.7±0.2.

As intended herein, in step a) the expression v/v is the abbreviation of volume per volume, thus, for example, the proportion of two solvents within a mixture as measured by the volume occupied by each solvent. A mixture of acetonitrile/water 20/1 v/v means for example 20 Liters of acetonitrile per 1 Liter of water.

As intended herein, in step e) the expression $C_1$-$C_4$ alcohol solvent means methanol, ethanol, iso-propanol, n-propanol, n-butanol, iso-butanol, sec-butanol, tert-butanol. The expression non polar solvents is referred to methylisobutylether, methylterbutylether, methylisobutylketone, tetrahydrofurane, n-heptane or solvents of equivalent polarity.

As intended herein, in step f) drying of the wet material under vacuum is performed to remove residual organic solvents from the product.

According to a preferred embodiment, the mixture is seeded at a temperature comprised in the range from 65° C. to 55° C. with Fluvastatin sodium salt of a crystalline form characterized by X-ray powder diffraction diagnostical peaks expressed in 2-Theta values (2θ) at 3.7±0.2, 11.2±0.2, 14.9±0.2, 15.9±0.2, 17.9±0.2, 18.4±0.2, 21.8±0.2, 25.7±0.2. Said seed can be prepared following one of the procedures described in the literature or by applying the process object of the present invention.

According to a preferred embodiment, in step c) the mixture is cooled to a temperature comprised in the range from 25° C. to 20° C. and stirred at this temperature for a time comprised in the range from 8 hours to 12 hours.

According to a preferred embodiment, in step e) the wet material is washed with 4-methylpentan-2-one (MIBK) or acetonitrile (ACN).

According to a preferred embodiment, in step f) the drying is performed for a period comprised in the range from 8 hours to 12 hours at a temperature of 40° C. and applying 3 mbar of residual vacuum.

According to a preferred embodiment, in step g) re-equilibration is performed at a temperature comprised in the range from 20° C. to 30° C. and a relative humidity (RH) of 60% for a time comprised between 12 hours and 3 days.

According to a preferred embodiment, in step e) the wet material is washed with 4-methylpentan-2-one, in step f) the drying is performed for a period comprised in the range from 8 hours to 12 hours at a temperature of 40° C. applying 3 mbar residual vacuum and in step g) the re-equilibration is performed at a temperature comprised in the range from 20° C. to 30° C. and a relative humidity (RH) of 60% for a time comprised between 12 hours and 3 days.

According to a preferred embodiment, the wet material isolated in step d) is obtained as Fluvastatin sodium salt of crystalline form characterized by X-ray powder diffraction diagnostical peaks expressed in 2-Theta values (2θ) at 6.9±0.2, 8.6±0.2, 12.0±0.2, 13.1±0.2, 17.7±0.2, 18.2±0.2.

Fluvastatin sodium salt of the crystalline form mentioned above can be used for preparing Fluvastatin sodium salt of a crystalline form characterized by X-ray powder diffraction diagnostical peaks expressed in 2-Theta values (2θ) at 3.7±0.2, 11.2±0.2, 14.9±0.2, 15.9±0.2, 17.9±0.2, 18.4±0.2, 21.8±0.2, 25.7±0.2, optionally applying the step from e) to g) described above.

EXPERIMENTAL SECTION

All the raw materials are commercially available, for example by Sigma-Aldrich.

Example 1—Preparation of FLVNa Form XIV or Form LXXXI (Sample E39-30-144)

To a round bottomed flask equipped with mechanical stirring containing FLVNa (15.0 g, 34.6 mmol), a mixture of ACN (300 mL, 20 V) and water (25.5 mL, 1.7 V) was added. The mixture was heated to dissolution (observed at 63° C.) and then stirred at this temperature for 30 min. The resulting solution was cooled down to 60° C. and seeded with FLVNa Form XIV/Form LXXXI. The mixture was then cooled down to 20-25° C. and stirred at this temperature for overnight. The slurry was filtered on a sintered funnel (porous no. 3). The wet material collected was submitted to XRPD analysis revealing the pattern characteristic of Form similar to Form B. After washing with MIBK (20 ml, 1.5 V) and drying at 40° C. under 3 mbar residual vacuum for overnight, the solid was exposed to 60% RH at 25° C. for 11 days affording FLVNa Form XIV/Form LXXXI (13.5 g, Y=90%).

Figure 7:
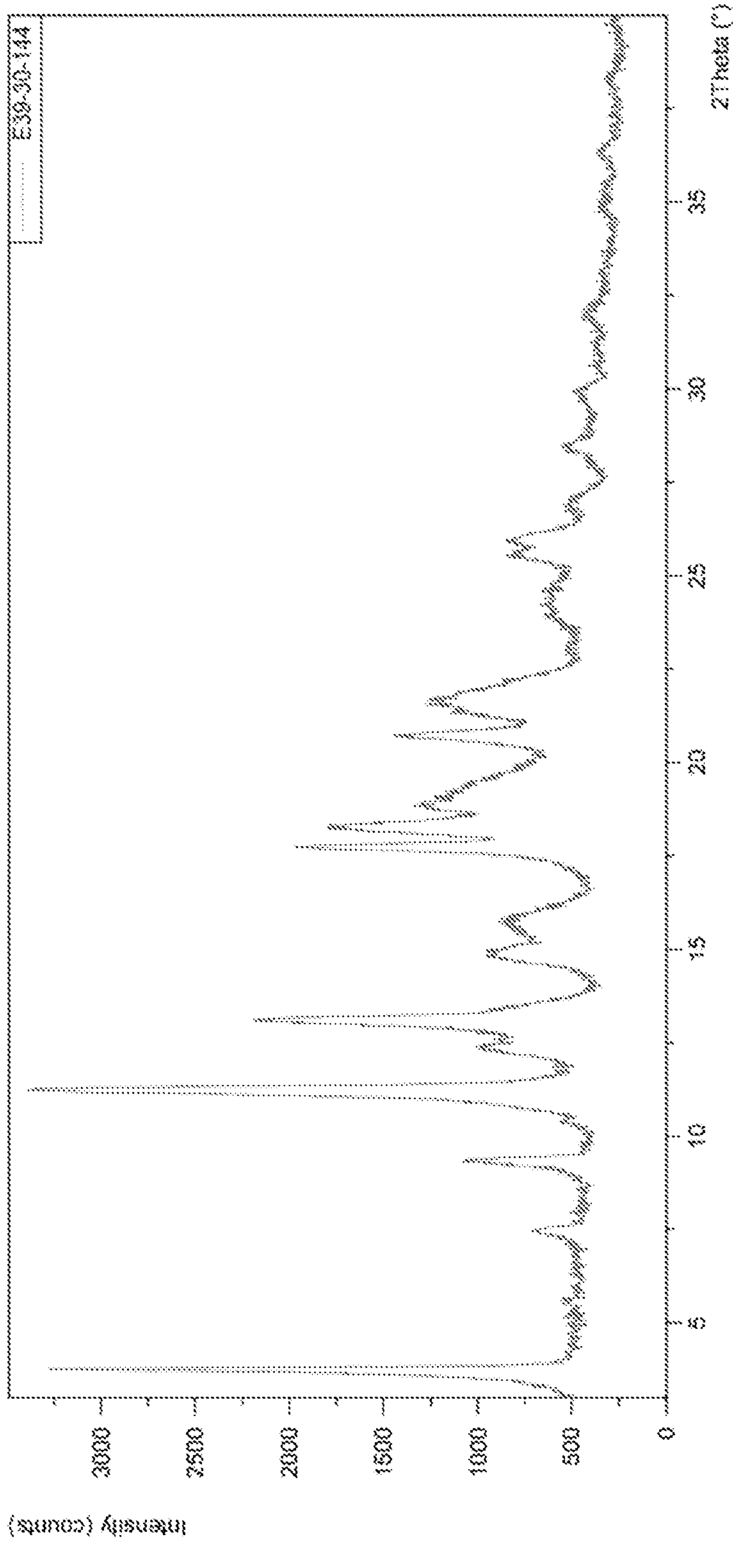
FIG. 7: XRPD diffractogram of Fluvastatin sodium salt obtained in Example 1.

The XPRD diffractogram of sample E39-30-144 is reported in FIG. 7.

Example 2—Preparation of FLVNa Form XIV or Form LXXXI (Sample E39-30-148)

To a round bottomed flask equipped with mechanical stirring containing FLVNa (15.0 g, 34.6 mmol), a mixture of ACN (300 mL, 20 V) and water (25.5 mL, 1.7 V) was added. The mixture was heated to dissolution (observed at 65° C.) and stirred at this temperature for 30 min. The resulting solution was cooled down to 60° C. and stirred at this temperature for 1 h before seeding with FLVNa Form XIV/Form LXXXI. The resulting mixture was stirred at 60° C. for 1 additional hour and then cooled down to 25° C. in 2.5 h. The slurry was stirred at 25° C. for overnight and then filtered on a sintered funnel (porous no. 3). Crystalline Form similar to Form B was obtained from the XRPD analysis of the wet solid. The wet cake was washed with MIBK (20 ml, 1.5 V). After drying at 40° C. under vacuum (ca 3 mbar residual pressure) for overnight, the solid was exposed to 60% RH at 25° C. for 3 days affording FLVNa Form XIV/Form LXXXI (13.1 g, Y=87%).

Figure 8:
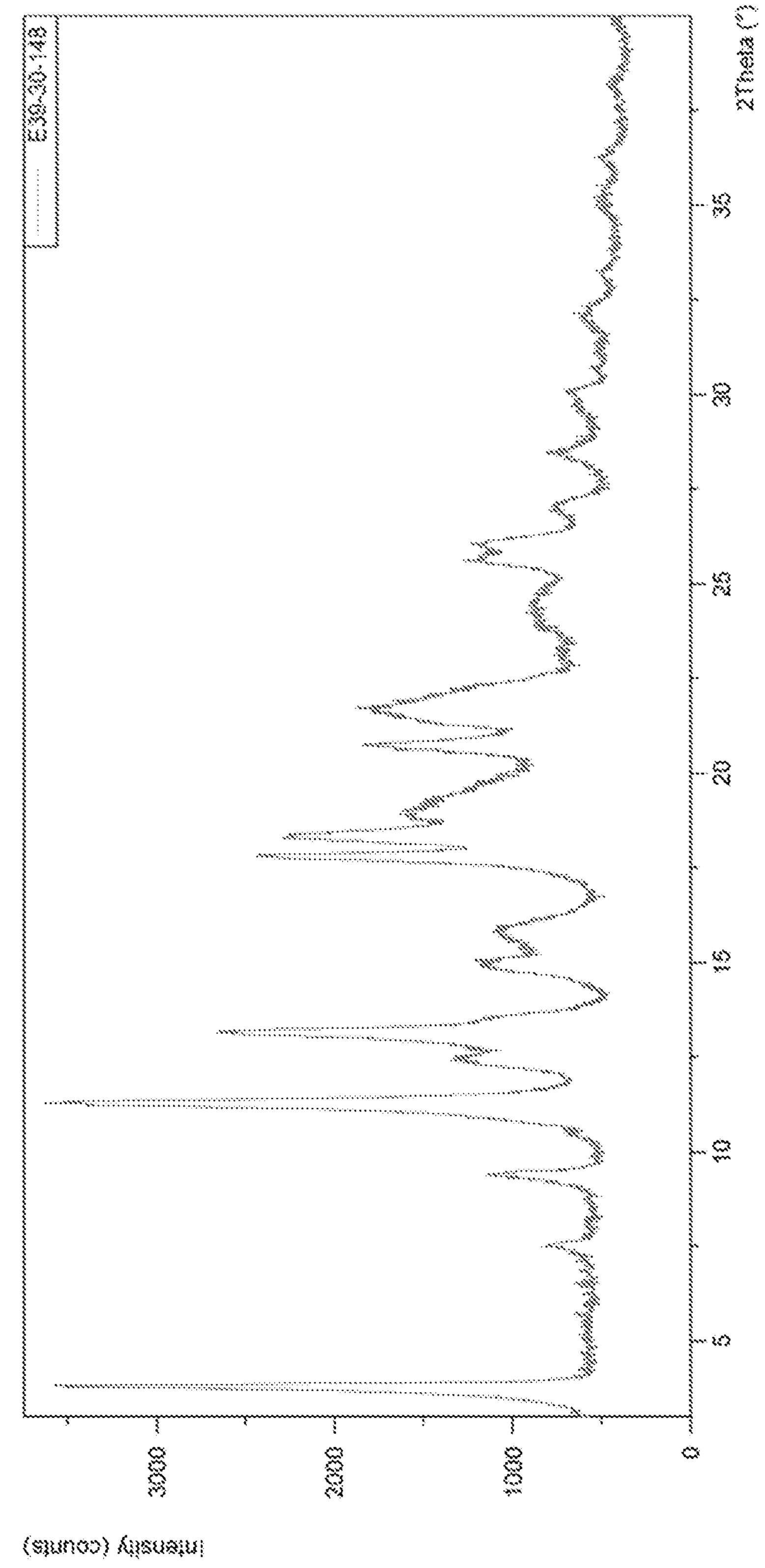
FIG. 8: XRPD diffractogram of Fluvastatin sodium salt obtained in Example 2.

The XPRD diffractogram of sample E39-30-148 is reported in FIG. 8.

Example 3—Preparation of FLVNa Form XIV or Form LXXXI (Sample E39-30-153)

To a round bottomed flask equipped with mechanical stirring containing FLVNa (15.0 g, 34.6 mmol), a mixture of ACN (300 mL, 20 V) and water (25.5 mL, 1.7 V) was added. The batch was heated to dissolution (observed at 66° C.) and stirred at this temperature for 1 h. The resulting solution was seeded with FLVNa Form XIV/Form LXXXI at 62° C. and stirred at this temperature for 1 h. The mixture was then cooled down to 25° C. in 2.5 h and stirred at this temperature for overnight. After filtration on a sintered funnel (porous no. 3), the wet cake was washed with MIBK (20 ml, 1.5 V). The solid was dried at 40° C. under vacuum (ca 3 mbar residual pressure) for overnight and then exposed to 60% RH at 25° C. for four days affording FLVNa Form XIV/Form LXXXI (12.9 g, Y=86%).

Figure 9:
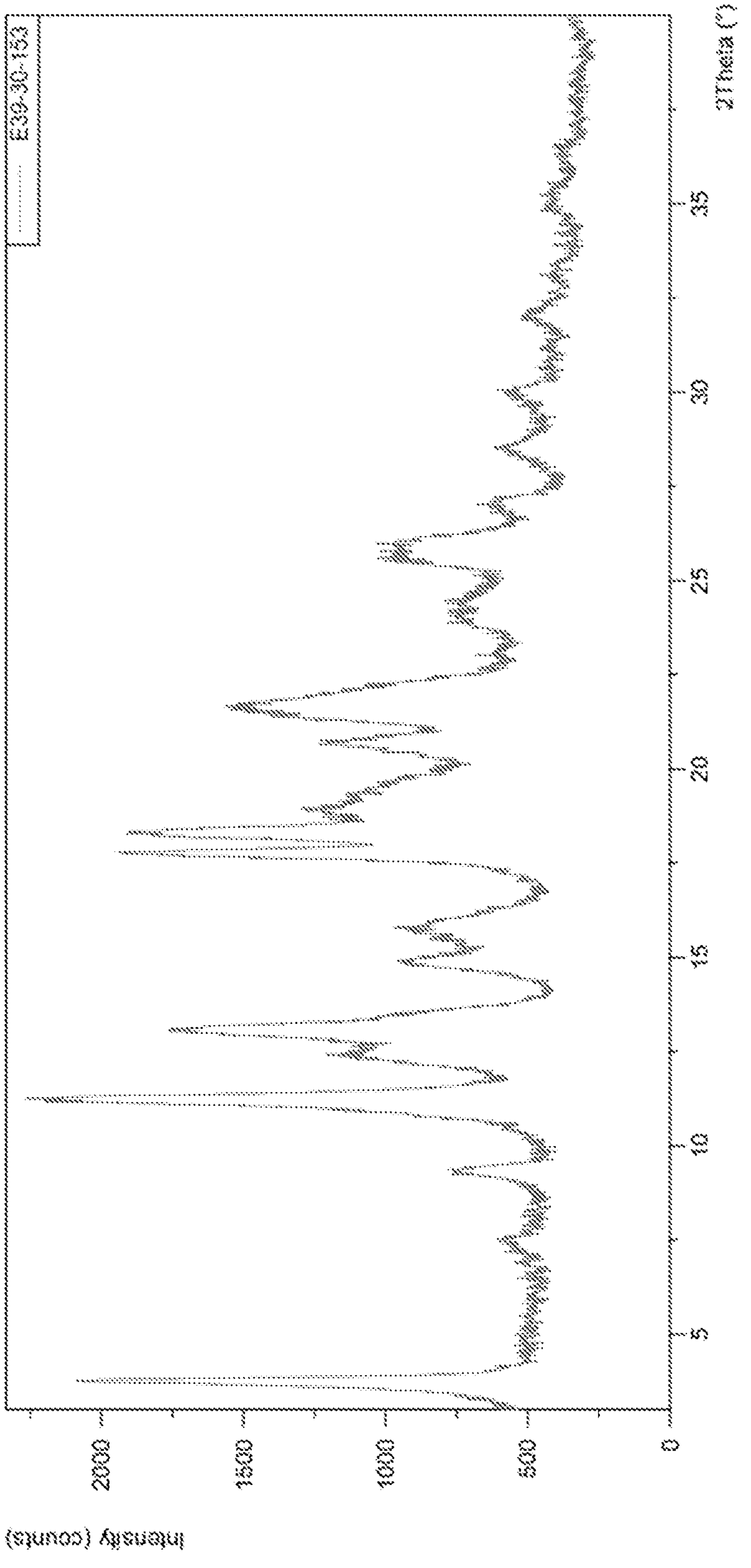
FIG. 9: XRPD diffractogram of Fluvastatin sodium salt obtained in Example 3.

The XPRD diffractogram of sample E39-30-153 is reported in FIG. 9.

Example 4—Preparation of FLVNa Form XIV or Form LXXXI (Sample E39-30-158)

To a round bottomed flask equipped with mechanical stirring containing FLVNa (15.0 g, 34.6 mmol), a mixture of ACN (300 mL, 20 V) and water (25.5 mL, 1.7 V) was added. The batch was heated to 66° C. and stirred at this temperature for 30 min (dissolution observed). The solution was cooled down to 60° C., stirred at this temperature for 1 h and then seeded with FLVNa Form XIV/Form LXXXI. The resulting mixture was stirred at 60° C. for 1 additional hour before cooling down to 25° C. in 2.5 h. The slurry was stirred at this temperature for overnight, filtered on a sintered funnel (porous no. 3) and the wet solid was washed with MIBK (20 ml, 1.5 V). After drying at 40° C. under vacuum (ca 3 mbar residual pressure) the solid was exposed to 60% RH at 25° C. for overnight affording FLVNa Form XIV/Form LXXXI (13.8 g, Y=92%).

Figure 10:
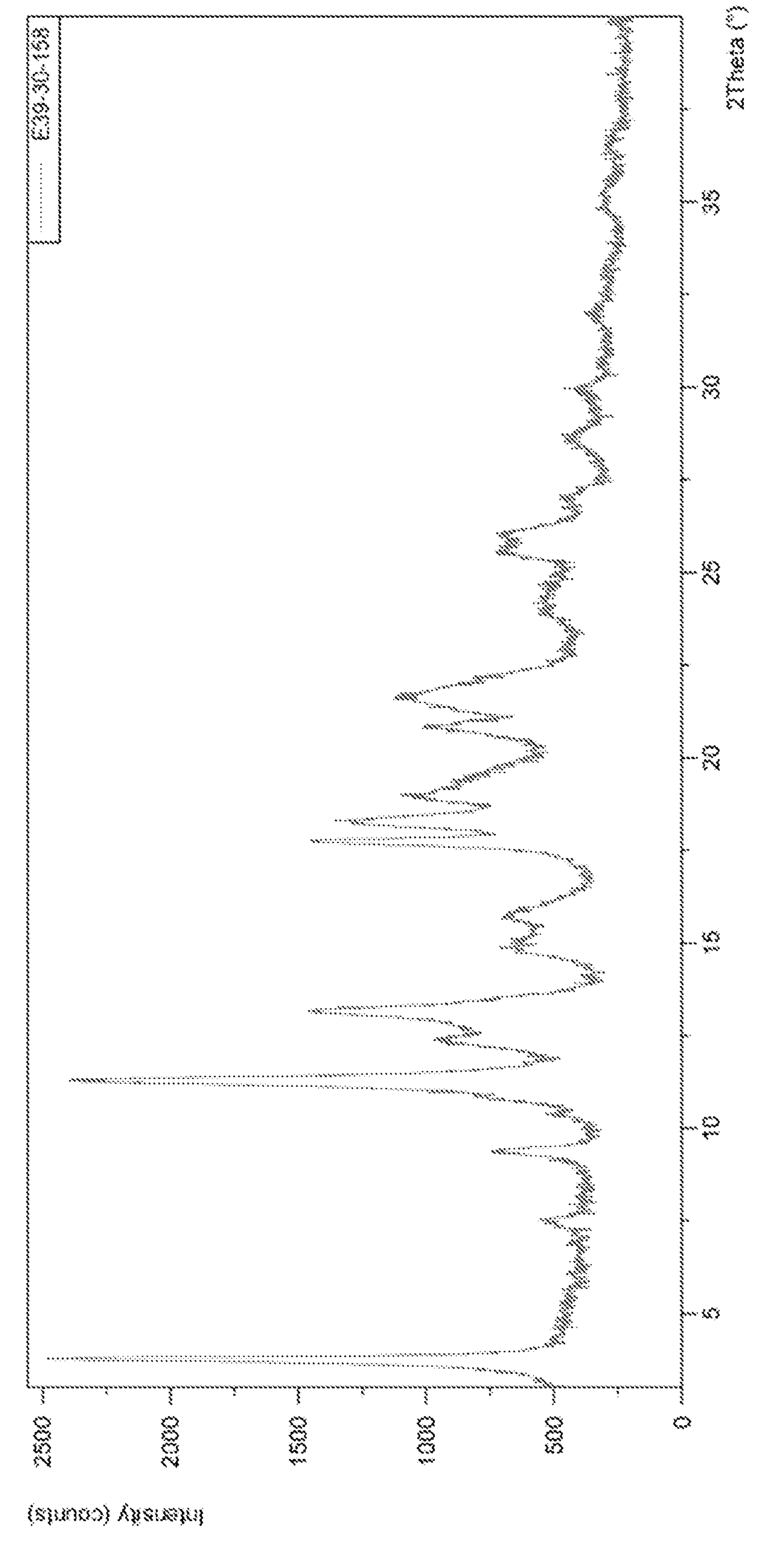
FIG. 10: XRPD diffractogram of Fluvastatin sodium salt obtained in Example 4.

The XPRD diffractogram of sample E39-30-158 is reported in FIG. 10.

Example 5—Preparation of FLVNa Form XIV or Form LXXXI (Sample E39-30-135A)

To a round bottomed flask equipped with mechanical stirring containing FLVNa (5.0 g, 11.5 mmol), a mixture of ACN (100 mL, 20 V) and water (8.5 mL, 1.7 V) was added. The batch was heated to dissolution (observed at 65° C.) and stirred at this temperature for 30 min. The solution was then cooled down to 62° C. and seeded with FLVNa form XIV/Form LXXXI. The resulting mixture was then cooled down to 20-25° C. and stirred at this temperature for overnight. The slurry was filtered on a sintered funnel (porous no. 3) and a portion of the wet cake was washed with ACN (4 mL, 2 V). The solid was dried at 40° C. under vacuum (ca 3 mbar residual pressure) for overnight and then exposed to 60% RH at 25° C. for 3 days affording FLVNa Form XIV/Form LXXXI.

Figure 11:
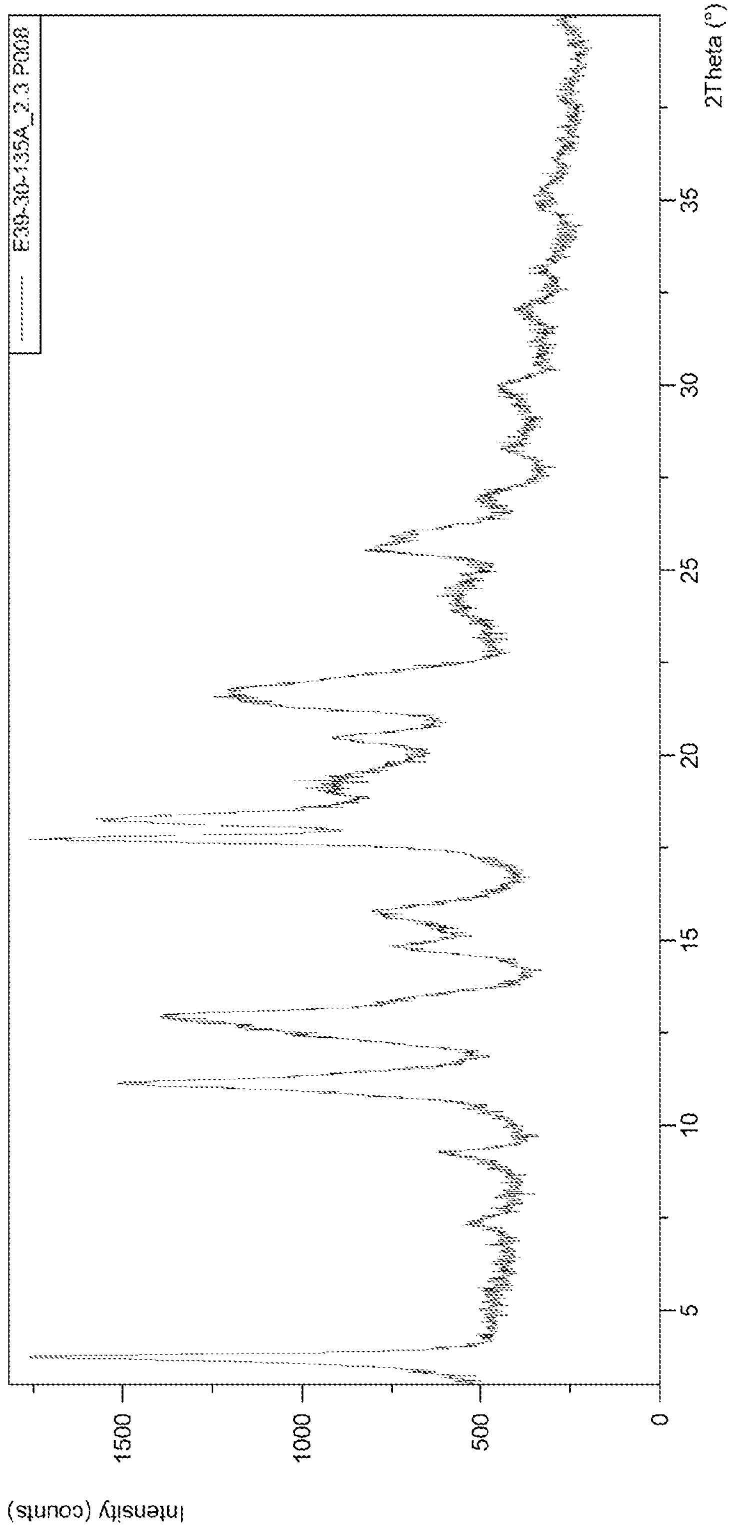
FIG. 11: XRPD diffractogram of Fluvastatin sodium salt obtained in Example 5.

The XPRD diffractogram of sample E39-30-135A is reported in FIG. 11.

Example 6—Preparation of FLVNa Form XIV or Form LXXXI (Sample E39-29-140A)—Comparative Example (not of Invention)

The procedure reported in Example 19 of U.S. Pat. No. 7,368,581 was reproduced, affording FLVNa Form B.

Example 7—Preparation of FLVNa Form XIV or Form LXXXI (Sample E39-29-148A)—Comparative Example (not of Invention)

The procedure reported in Example 19 of U.S. Pat. No. 7,368,581 was reproduced, affording FLVNa Form LXXX.

Example 8—Preparation of FLVNa Form XIV or Form LXXXI (Sample E39-29-147)—Comparative Example (not of Invention)

The procedure reported in Example 21 of U.S. Pat. No. 7,368,581 was reproduced, affording FLVNa Form LXXIX.

Example 9—Preparation of FLVNa Form XIV or Form LXXXI (Sample E39-29-152)—Comparative Example (not of Invention)

The procedure reported in Example 21 of U.S. Pat. No. 7,368,581 was reproduced, affording FLVNa Form XIV/Form LXXXI.

Example 10—Preparation of FLVNa Form XIV or Form LXXXI (Sample E39-29-158)—Comparative Example (not of Invention)

The procedure reported in Example 21 of U.S. Pat. No. 7,368,581 was reproduced, affording FLVNa Form XIV/Form LXXXI.

Example 11—Preparation of FLVNa Form XIV or Form LXXXI (Sample E39-29-140B)—Comparative Example (not of Invention)

The procedure reported in Example 20 of U.S. Pat. No. 7,368,581 was reproduced, affording FLVNa as a mixture of Form XIV and Form VII.

Example 12—Preparation of FLVNa Form XIV or Form LXXXI (Sample E39-29-148B)—Comparative Example (not of Invention)

The procedure reported in Example 20 of U.S. Pat. No. 7,368,581 was reproduced, but no product precipitation was observed.

Example 13 - Table comparing the results of the Experiments reported above

| Experiment # | Experimental Method | FLVNa XRPD (dry product) |
|---|---|---|
| E39-30-144 (Example 1) | Present application | Form XIV/Form LXXXI |
| E39-30-148 (Example 2) | Present application | Form XIV/Form LXXXI |
| E39-30-153 (Example 3) | Present application | Form XIV/Form LXXXI |
| E39-30-158 (Example 4) | Present application | Form XIV/Form LXXXI |
| E39-30-135A (Example 5) | Present application | Form XIV/Form LXXXI |
| E39-29-140A (Example 6) | EX19 U.S. Pat. No. 7,368,581 | Form B |
| E39-29-148A (Example 7) | EX19 U.S. Pat. No. 7,368,581 | Form LXXX |
| E39-29-147 (Example 8) | EX21 U.S. Pat. No. 7,368,581 | Form LXXIX |
| E39-29-152 (Example 9) | EX21 U.S. Pat. No. 7,368,581 | Form XIV/Form LXXXI |
| E39-29-158 (Example 10) | EX21 U.S. Pat. No. 7,368,581 | Form XIV/Form LXXXI |
| E39-29-140B (Example 11) | EX20 U.S. Pat. No. 7,368,581 | Form XIV + Form VII |
| E39-29-148B (Example 12) | EX20 U.S. Pat. No. 7,368,581 | no crisyallization |

Example 14—XPRD Method

Diffraction measurements were performed at ambient conditions on a PANalytical X'Pert PRO θ-θ diffractometer of 240 mm of radius in reflection geometry, equipped with Cu Kα radiation and a PIXcel detector, operated at 45 kV and 40 mA. Each sample was mounted on a zero-background silicon holder and allowed to spin at 0.25 rev/s during the data collection. The measurement angular range was 3.0-40.0° (2θ) with a step size of 0.013°. The scanning speed was 0.328°/s (10.20 s/step or 0.082°/s (40.80 s/step).

The invention claimed is:

1. A process for preparing a crystalline form of fluvastatin sodium salt of formula (I):

(I)

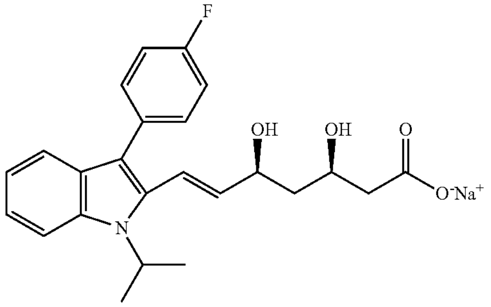

wherein said crystalline form of fluvastatin sodium salt is characterized by X-ray powder diffraction diagnostical peaks expressed in 2-Theta values (2θ) at 3.7±0.2, 11.2±0.2, 14.9±0.2, 15.9±0.2, 17.9±0.2, 18.4±0.2, 21.8±0.2, 25.7±0.2;

comprising:

a) dissolving fluvastatin sodium salt of any crystalline form and/or amorphous form by heating said salt in a mixture of acetonitrile/water 20/1 to 20/2.5 v/v, or alternatively in a mixture of acetonitrile/water from 5/1 to 5/2 v/v followed by dilution with acetonitrile to realize a final solvent ratio acetonitrile/water from 20/1 to 20/2.5 v/v;

b) cooling the solution of step a) to a temperature of from 65° C. to 35° C. to promote fluvastatin sodium salt crystallization and, optionally, seeding the mixture with the above mentioned crystalline form of fluvastatin sodium salt;

c) further cooling the mixture obtained in step b) to a temperature of from 35° C. to 15° C. and stirring the slurry at said temperature for a time ranging from 1 hour to 3 days;

d) isolating the fluvastatin sodium salt wet material by filtration or centrifugation of the slurry of step c), wherein said fluvastatin sodium salt has a crystalline form optionally characterized by X-ray powder diffraction diagnostical peaks expressed in 2-Theta values (2θ) at 6.9±0.2, 8.6±0.2, 12.0±0.2, 13.1±0.2, 17.7±0.2, 18.2±0.2;

wherein the process further comprises:

e) washing of the wet material obtained in step d) with acetonitrile, a $C_1$-$C_4$ alcohol solvent or a non-polar solvent;

f) drying the wet solid obtained in step e) under vacuum with a residual pressure range of from 1 mbar to 500 mbar at a temperature of from 20° C. to 60° C. and for a time ranging from 1 hour to 3 days;

g) re-equilibrating the crystalline form obtained in step f) by treating the solid for a time of from 1 hour to 11 days at a temperature of from 15° C. to 35° C. under relative humidity (RH) of from 40% and 80% to provide fluvastatin sodium salt in a crystalline form characterized by X-ray powder diffraction diagnostical peaks expressed in 2-Theta values (2θ) at 3.7±0.2, 11.2±0.2, 14.9±0.2, 15.9±0.2, 17.9±0.2, 18.4±0.2, 21.8±0.2, 25.7±0.2.

2. The process of claim 1, wherein in step b) the mixture is seeded at a temperature of from 65° C. to 55° C. with fluvastatin sodium salt of a crystalline form characterized by X-ray powder diffraction diagnostical peaks expressed in 2-Theta values (2θ) at 3.7±0.2, 11.2±0.2, 14.9±0.2, 15.9±0.2, 17.9±0.2, 18.4±0.2, 21.8±0.2, 25.7±0.2.

3. The process of claim 1, wherein in step c) the slurry is cooled to a temperature of from 25° C. to 20° C. and stirred at this temperature for a time of from 8 hours to 12 hours.

4. The process of claim 1, wherein in step e) the wet material is washed with 4-methylpentan-2-one.

5. The process of claim 1, wherein in step e) the wet material is washed with acetonitrile.

6. The process of claim 1, wherein in step f) the drying is performed for a time of from 8 hours to 12 hours at a temperature of 40° C. applying 3 mbar of residual vacuum.

7. The process of claim 1, wherein in step g) the re-equilibration is performed at a temperature of from 20° C. to 30° C. and at a relative humidity (RH) of 60% for a time of between 12 hours and 3 days.

8. The process of claim 1, wherein in step e) the wet material is washed with 4-methylpentan-2-one, in step f) the drying is performed for from 8 hours to 12 hours at a temperature of 40° C. applying 3 mbar of residual vacuum and in step g) the re-equilibration is performed at a temperature of from 20° C. to 30° C. and at a relative humidity (RH) of 60% for a time of between 12 hours and 3 days.

9. The process of claim 1, wherein the wet material isolated in step d) is obtained as fluvastatin sodium salt of crystalline form characterized by X-ray powder diffraction diagnostical peaks expressed in 2-Theta values (2θ) at 6.9±0.2, 8.6±0.2, 12.0±0.2, 13.1±0.2, 17.7±0.2, 18.2±0.2.

10. A crystalline form of fluvastatin sodium salt characterized by X-ray powder diffraction diagnostical peaks expressed in 2-Theta values (2θ) at 6.9±0.2, 8.6±0.2, 12.0±0.2, 13.1±0.2, 17.7±0.2, 18.2±0.2.

* * * * *